United States Patent
Flynn et al.

(10) Patent No.: US 7,856,082 B2
(45) Date of Patent: Dec. 21, 2010

(54) SYSTEM AND METHOD FOR OPTIMIZATION OF A RADIATION THERAPY PLAN IN THE PRESENCE OF MOTION

(75) Inventors: Ryan T. Flynn, Iowa Cita, IA (US); Thomas R. Mackie, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 113 days.

(21) Appl. No.: 12/440,055

(22) PCT Filed: Feb. 27, 2008

(86) PCT No.: PCT/US2008/055147

§ 371 (c)(1),
(2), (4) Date: Mar. 5, 2009

(87) PCT Pub. No.: WO2008/106522

PCT Pub. Date: Sep. 4, 2008

(65) Prior Publication Data

US 2010/0189220 A1    Jul. 29, 2010

Related U.S. Application Data

(60) Provisional application No. 60/891,859, filed on Feb. 27, 2007.

(51) Int. Cl.
*A61N 5/10* (2006.01)
(52) U.S. Cl. .............................. 378/65; 378/69; 378/95; 250/492.1
(58) Field of Classification Search ................... 378/65, 378/69, 95; 250/492.1
See application file for complete search history.

(56) References Cited

U.S. PATENT DOCUMENTS 4,276,477 A    6/1981    Enge (Continued)

FOREIGN PATENT DOCUMENTS

DE    19907098 A1    8/2000

(Continued)

OTHER PUBLICATIONS

International Search Report, PCT Application No. PCT/US2008/055104, dated Jul. 17, 2008, ISA/EPO, 2280 HV Rijswijk, NL.

(Continued)

*Primary Examiner*—Edward J Glick
*Assistant Examiner*—Thomas R Artman
(74) *Attorney, Agent, or Firm*—Boyle Fredrickson, S.C.

(57) ABSTRACT

A computer-implemented method for optimizing a radiation treatment plan for a radiotherapy machine providing independently controlled radiation along a plurality of rays j directed toward a patient and configured to account for the effects of patient motion. The method includes generating a probability distribution function quantitatively expressing patient motion, identifying a prescribed total dose $D_i^p$ at the voxels i in a treatment area, assigning a fluence value $w_j$ for each ray j based on an iterative function, calculating an actual total dose $D_i^d$ produced each voxel i within the assigned fluence values and calculating an expectation value of the dose per energy fluence, $\langle d_{ij} \rangle$ based on the actual total dose $D_i^d$ and the probability distribution function.

20 Claims, 5 Drawing Sheets

U.S. PATENT DOCUMENTS

| | | | |
|---|---|---|---|
| 5,317,616 | A | 5/1994 | Swerdloff et al. |
| 5,394,452 | A | 2/1995 | Swerdloff et al. |
| 5,442,675 | A | 8/1995 | Swerdloff et al. |
| 5,528,650 | A | 6/1996 | Swerdloff et al. |
| 5,548,627 | A | 8/1996 | Swerdloff et al. |
| 5,625,663 | A | 4/1997 | Swerdloff et al. |
| 5,661,773 | A | 8/1997 | Swerdloff et al. |
| 5,668,371 | A | 9/1997 | Deasy et al. |
| 5,673,300 | A | 9/1997 | Reckwerdt et al. |
| 5,724,400 | A | 3/1998 | Swerdloff et al. |
| 5,802,136 | A | 9/1998 | Carol |
| 6,345,114 | B1 | 2/2002 | Mackie et al. |
| 6,385,286 | B1 | 5/2002 | Fitchard et al. |
| 6,438,202 | B1 | 8/2002 | Olivera et al. |
| 6,560,311 | B1 | 5/2003 | Shepard et al. |
| 6,618,467 | B1 | 9/2003 | Ruchala |
| 6,636,622 | B2 | 10/2003 | Mackie et al. |
| 6,661,870 | B2 | 12/2003 | Kapatoes et al. |
| 6,731,970 | B2 | 5/2004 | Scholssbauer et al. |
| 6,915,005 | B1 | 7/2005 | Ruchala et al. |
| 7,046,831 | B2 | 5/2006 | Ruchala et al. |
| 7,186,986 | B2 | 3/2007 | Hinderer et al. |
| 7,206,377 | B2 * | 4/2007 | Svatos .......................... 378/65 |
| 7,207,715 | B2 | 4/2007 | Yue |
| 7,302,038 | B2 | 11/2007 | Mackie |
| 7,369,645 | B2 * | 5/2008 | Lane ............................ 378/65 |
| 2002/0136439 | A1 | 9/2002 | Ruchala et al. |
| 2003/0160189 | A1 | 8/2003 | Matsuda |
| 2003/0198319 | A1 | 10/2003 | Toth et al. |
| 2005/0123092 | A1 | 6/2005 | Mistretta et al. |
| 2005/0197564 | A1 | 9/2005 | Dempsy |
| 2006/0226372 | A1 | 10/2006 | Yanagisawa |
| 2006/0285639 | A1 | 12/2006 | Olivera et al. |
| 2007/0029510 | A1 | 2/2007 | Hermann |
| 2007/0036267 | A1 | 2/2007 | Becker et al. |
| 2007/0041494 | A1 | 2/2007 | Ruchala et al. |
| 2007/0041495 | A1 | 2/2007 | Olivera et al. |
| 2007/0041496 | A1 | 2/2007 | Olivera et al. |
| 2007/0041497 | A1 | 2/2007 | Schnarr et al. |
| 2007/0041498 | A1 | 2/2007 | Olivera et al. |
| 2007/0041499 | A1 | 2/2007 | Lu et al. |
| 2007/0041500 | A1 | 2/2007 | Olivera et al. |
| 2007/0043286 | A1 | 2/2007 | Lu et al. |
| 2007/0076846 | A1 | 4/2007 | Ruchala et al. |
| 2007/0104316 | A1 | 5/2007 | Ruchala et al. |
| 2007/0195922 | A1 | 8/2007 | Mackie et al. |
| 2007/0195929 | A1 | 8/2007 | Ruchala et al. |
| 2007/0195930 | A1 | 8/2007 | Kapotoes et al. |
| 2007/0242801 | A1 | 10/2007 | Mackie et al. |

FOREIGN PATENT DOCUMENTS

| | | |
|---|---|---|
| EP | 0986070 A | 3/2000 |
| EP | 1045399 A | 10/2000 |
| JP | 2000 214298 A | 8/2000 |
| WO | WO02/07817 A | 1/2002 |
| WO | WO 02/41948 | 5/2002 |
| WO | WO2005/004168 A | 1/2005 |
| WO | WO2007/021226 A | 2/2007 |

OTHER PUBLICATIONS

International Search Report, PCT Application No. PCT/US2008/055070, dated Jul. 17, 2008, ISA/EPO, 2280 HV Rijswijk, NL.

International Search Report, PCT Application No. PCT/US2008/055069, dated Jul. 17, 2008, ISA/EPO, 2280 HV Rijswijk, NL.

International Search Report, PCT Application No. PCT/US2008/055161, dated Jul. 17, 2008, ISA/EPO, 2280 HV Rijswijk, NL.

International Search Report, PCT Application No. PCT/US2008/055083, dated Jul. 17, 2008, ISA/EPO, 2280 HV Rijswijk, NL.

International Search Report, PCT Application No. PCT/US2008/055096 dated Jul. 17, 2008, ISA/EPO, 2280 HV Rijswijk, NL.

International Search Report, PCT Application No. PCT/US2008/055090 dated Jul. 17, 2008, ISA/EPO, 2280 HV Rijswijk, NL.

International Search Report, PCT Application No. PCT/US2008/055147, dated Jul. 25, 2008, ISA/EPO, 2280 HV Rijswijk, NL.

Baumert, BG, et al., Dose conformation of intensity-modulated stereotactic photon beams, proton beams, and intensity-modulated proton beams for intracranial lesions, Int. J. Radiat. Oncol. Biol. Phys., 2005, 60:1314-1324, Elsevier, Amsterdam, Netherlands.

Deasy, Jo, et al., Distal edge tracking: a proposed delivery method for conformal proton therapy using intensity modulation, 1997, pp. 406-409, Proceedings of the XIIth International Congress on Computers in Radiotherapy May 27-30, 1997, Salt Lake City, IEEE Publishing, Los Alamitos California. USA.

Deasy, Jo, A proton dose calculation algorithm for conformal therapy simulations based on Moliere theory of lateral deflections, Med. Phys., Apr. 1998, 25:476-483, American Association of Physical Medicine, New York, New York.

Lomax, AJ, Intensity modulation methods for proton radiotherapy, Phys. Med. Biol., 1999 44:185-205, IOP Publishing Ltd., Bristol, UK.

Lomax, AJ, et al. Intensity modulated proton therapy: A clinical example, Mar. 2001, Med. Phys. 28:317-324, American Association of Physical Medicine, New York, New York.

Lomax, AJ, Compensated and intensity-modulated proton therapy, in Palta J, and Mackie TR (eds), Intensity Modulated Radiation Therapy: The State of the Art, Nov. 2004, pp. 787-828, Medical Physics Publishing Madison, WI.

Lomax, AJ, et al., Treatment planning and verification of proton therapy using spot scanning: initial experiences. 2004a, Med. Phys. 31:3150-3157, American Association of Physical Medicine, New York, New York.

Lomax, AJ, et al., The clinical potential of intensity modulated proton therapy, 2004b, Z. Med. Phys. 14:147-154 Elsevier, Amsterdam, Netherlands.

Kanai, T, et al., Spot scanning system for proton radiotherapy, Jul./Aug. 1980, Med. Phys 7:365-369, American Association of Physical Medicine, New York, New York.

Moyers MF, (Proton therapy, Van Dyk (ed), The Modem Technology of Radiation Oncology, 1999, pp. 823-869, Medical Physics Publishing, Madison, WI.

Nill, S, et al., Inverse planning of intensity modulated proton therapy, 2004, Z Med. Phys. 14:35-40, Elsevier, Amsterdam, Netherlands.

Oelfke U, et al., Intensity modulated radiotherapy with charged particle beams: Studies of inverse treatment planning for rotation therapy. Jun. 2000, Med. Phys, 27:1246-1257, American Association of Physical Medicine, New York, New York.

Paganetti H, Proton Therapy: A Workshop Handout. 2005, Private Communication, Massachusetts General Hospital, Boston, MA.

Sampayan S, et al. Development of a compact radiography accelerator using dielectric wall accelerator technology, Jun. 6, 2005, Proceed. Int. Pulsed Power Conf. Monterey, CA, Lawrence Livermore Laboratory, Livermore, CA.

Wilson RW., Radiological use of fast protons. Nov. 1946, Radiology 47:487-491, Radiological Society of North America, Easton, Pennsylvania.

Yu C., Intensity modulated arc therapy with dynamic multileaf collimation: an alternative to tomotherapy, 1995, Phys. Med. Biol. 40:1435-1449, IOP Publishing Ltd., Bristol, UK.

Anferov V., Combined X-Y scanning magnet for conformal proton radiation therapy, Med. Phys. , Mar. 2005, 32:815-818, American Association of Physical Medicine, New York, New York.

Goitlein, M., Beam scanning for heavy charged particle radiotherapy, Nov./Dec. 1983, Med. Phys. 10 (6) pp. 831-840, American Association of Physical Medicine, New York, New York.

* cited by examiner

SYSTEM AND METHOD FOR OPTIMIZATION OF A RADIATION THERAPY PLAN IN THE PRESENCE OF MOTION

CROSS-REFERENCE TO RELATED APPLICATIONS

This application claims the benefit of U.S. Provisional Application 60/891,859, filed Feb. 27, 2007, and PCT Application PCT/US2008/055147, filed Feb. 27, 2008, the disclosures of which are incorporated herein by reference.

STATEMENT REGARDING FEDERALLY SPONSORED RESEARCH OR DEVELOPMENT

This invention was made with United States government support awarded by the following agency: NIH CA088960. The United States government has certain rights in this invention.

BACKGROUND OF THE INVENTION

The present invention relates generally to radiation therapy planning for the treatment of tumors and is suitable for radiation therapy machines providing independent intensity modulated narrow beams of radiation. More specifically, the present invention relates to a system and method for generating intensity maps for intensity modulated therapy (IMRT) in which the effects of patient motion are taken into account.

Radiation therapy involves the treatment of tumorous tissue with high energy radiation according to a treatment plan. The treatment plan controls the radiation's placement and dose level so that the tumorous tissue receives a sufficient dose of radiation while the radiation to surrounding and adjacent non-tumorous tissue is minimal.

Intensity modulated radiation therapy treats a patient with multiple rays of radiation each of which may be independently controlled in intensity and/or energy. The rays are directed from different angles about the patient and combine to provide a desired dose pattern. Typically, the radiation source consists of either high-energy X-rays, electrons from certain linear accelerators, or gamma rays from highly focused radioisotopes such as $Co^{60}$.

Methods of producing intensity modulated rays of radiation are well known in the art and include the stop and shoot method, (Xia, P., Verhey, L. J., "Multileaf Collimation Leaf Sequencing Algorithm for Intensity Modulated Beams with Multiple Static Segments," Medical Physics, 25:1424-34 (1998)), the sliding window technique (Bortfeld, et al., "Realization and Verification of Three-Dimensional Conformal Radiotherapy With Modulated Fields," Int'l J. Radiat. Oncol. Biol. Phys., 30:899-908 (1994)), intensity modulated arc therapy, (Yu, C. X., "Intensity-Modulated Arc Therapy With Dynamic Multileaf Collimation: An Alternative to Tomotherapy," Physics in Medicine & Biology, 40:1435-49 (1995)), and sequential (axial) tomotherapy, (Carol, et al., "The Field-Matching Problem as it Applies to the Peacock Three Dimensional Conformal System for Intensity Modulation," Int'l J. Radiat. Oncol. Biol. Phys., 34:183-87 (1996)).

One highly accurate IMRT method uses a planar fan beam which orbits the patient in the plane of the beam to treat a single slice of the patient at a time. Prior to reaching the patient, the fan beam is passed through a multileaf collimator (MLC) consisting of a series of opaque leaves. As the radiation source rotates around the patient, the tungsten leaves move into and out of the radiation beam modulating the intensity of individual rays of the fan beam.

An intensity value for each ray of the fan beam at each angle of the fan beam about the patient and for each slice of the patient is defined by a treatment sinogram. The treatment sinogram is prepared by a physician based on a dose map indicating the amount of radiation dose and its location throughout the patient. This type of treatment sinogram assumes that the location of the patient and the target area remains static.

However, neither the location of the patient nor the location a target area is usually static. Movement of the target area may occur based on, for example, patient breathing, digestive processes, slight variations in patient positioning, etc. Accordingly, even considering the accuracy of the IMRT method, a target area or portions of a patient area may not receive the correct dosage designated by a treatment plan.

What is needed is a system and method for the determination of intensity maps for intensity modulated radiation therapy in which the effects of patient motion are taken into account. What is further needed is such a system and method wherein an objective function is minimized using a generalized version of a linear least squares method which reduces back to the original treatment sinogram in the idealized case where there is no patient motion.

SUMMARY OF THE INVENTION

One exemplary embodiment provides a computer-implemented method for optimizing a radiation treatment plan for a radiotherapy machine providing independently controlled radiation along a plurality of rays j directed toward a patient and configured to account for the effects of patient motion. The method includes generating a probability distribution function quantitatively expressing patient motion, identifying a prescribed total dose $D_i^p$ at the voxels i in a treatment area and assigning a fluence value $w_j$ for each ray j, based on an iterative function:

$$w_j^{(k+1)} = w_j^k \frac{N \sum_{m=1}^{M} C_m \sum_{i \in \tau_m} \langle d_{ij} \rangle D_i^p}{(N-1) \sum_{m=1}^{M} C_m \sum_{i \in \tau_m} \langle D_{ij}^{d^k} \rangle \langle d_{ij} \rangle + \sum_{m=1}^{M} C_m \sum_{i \in \tau_m} \langle d_{ij} D_i^{d^k} \rangle}, \quad (6)$$

where N is the number of treatment fractions, $D_i^p$ is the planned dose to voxel i, $D_i^{d^k}$ is the motion-uncorrected dose to voxel i for iteration k, and $C_m$ is a weighting factor assigned to structure m, which may be either a tumor or sensitive area. The method further includes calculating an actual total dose $D_i^d$ produced in each voxel i within the assigned fluence values and calculating an expectation value of the dose per energy fluence, $\langle d_{ij} \rangle$ based on the actual total dose $D_i^d$ and the probability distribution function.

Another exemplary embodiment provides a system for optimizing a radiation treatment plan by providing independently controlled radiation along a plurality of rays j directed toward a patient configured to account for the effects of patient motion. The system includes a radiation source configured to generate the plurality of rays, a shutter system configured to attenuate the rays generated by the radiation source, and a computer system configured to control the radiation source and the shutter system to implement a radiation treatment plan to account for the effects of patient motion. The treatment plan includes the steps of generating a probability distribution function quantitatively expressing patient motion, identifying a prescribed total dose $D_i^p$ at the voxels i in a treatment area, and assigning a fluence value $w_j$ for each ray j, based on an iterative function:

$$w_j^{(k+1)} = w_j^k \frac{N \sum_{m=1}^{M} C_m \sum_{i \in \tau_m} \langle d_{ij} \rangle D_i^p}{(N-1) \sum_{m=1}^{M} C_m \sum_{i \in \tau_m} \langle D_i^{d^k} \rangle \langle d_{ij} \rangle + \sum_{m=1}^{M} C_m \sum_{i \in \tau_m} \langle d_{ij} D_i^{d^k} \rangle}, \quad (6)$$

where N is the number of treatment fractions, $D_i^p$ is the planned dose to voxel i, $D_i^{d^k}$ is the motion-uncorrected dose to voxel i for iteration k, and $C_m$ is a weighting factor assigned to structure m, which may be either a tumor or sensitive area. The step d further include calculating an actual total dose $D_i^d$ produced each voxel i within the assigned fluence values, and calculating an expectation value of the dose per energy fluence, $\langle d_{ij} \rangle$ based on the actual total dose $D_i^d$ and the probability distribution function.

Yet another exemplary embodiment provides a computer-implemented method for optimizing a radiation treatment plan for a radiotherapy machine providing independently controlled radiation along a plurality of rays j directed toward a patient configured to account for the effects of patient motion. The method includes generating a probability distribution function quantitatively expressing patient motion, identifying a prescribed total dose $D_i^p$ at the voxels i in a treatment area and assigning a fluence value $w_j$ for each ray j, based on an iterative function:

$$w_j^{(k+1)} = w_j^k \frac{N \sum_{m=1}^{M} C_m \sum_{i \in \tau_m} \langle d_{ij} \rangle D_i^p}{(N-1) \sum_{m=1}^{M} C_m \sum_{i \in \tau_m} \langle D_i^{d^k} \rangle \langle d_{ij} \rangle + \sum_{m=1}^{M} C_m \sum_{i \in \tau_m} \langle d_{ij} D_i^{d^k} \rangle}, \quad (6)$$

where N is the number of treatment fractions, $D_i^p$ is the planned dose to voxel i, $D_i^{d^k}$ is the motion-uncorrected dose to voxel i for iteration k, and $C_m$ is a weighting factor assigned to structure m, which may be either a tumor or sensitive area. calculating an expectation value of the dose per energy fluence, $\langle d_{ij} \rangle$ based on the actual total dose $D_i^d$ and the probability distribution function.

These particular features and advantages may apply to only some embodiments falling within the claims and thus do not define the scope of the invention.

DETAILED DESCRIPTION OF THE PREFERRED EMBODIMENT

Figure 1:
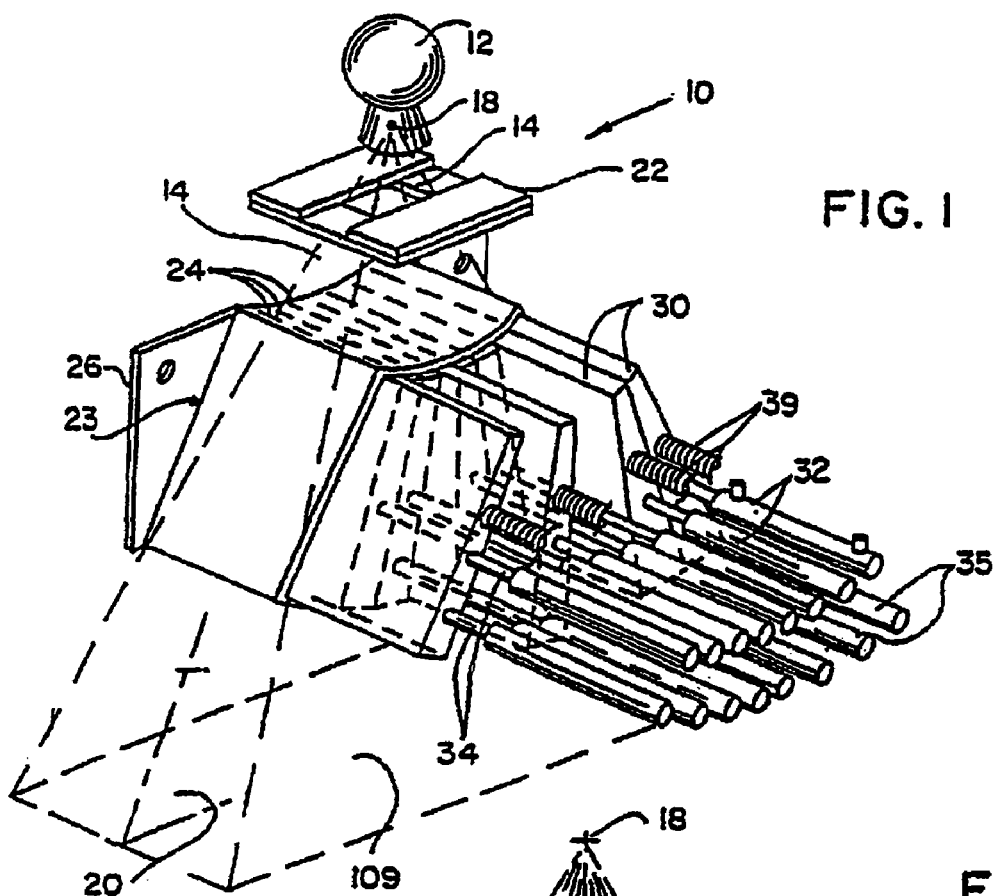
FIG. 1 is a perspective view of the shutter system assembly used in the present invention showing the shutter leaves and their associated actuators.

Referring to FIG. 1, such a radiation therapy machine 10 includes a radiation source 12 producing a generally conical radiation beam 14' emanating from a focal spot 18 and directed toward a patient 17 (not shown in FIG. 1). The conical radiation beam 14' is collimated by a rectangular opaque mask 16 constructed of a set of rectangular shutter system blades to form a generally planar radiation fan beam 14 centered about a radiation fan beam plane 20. Whereas the present application describes a multi-leaf collimator-type radiation therapy machine system, the system and method described herein may be used with any therapy machine configured to perform intensity modulated radiation therapy.

A shutter system 22 is centered in the radiation fan beam 14 and about the radiation fan beam plane 20 prior to the radiation beam being received by the patient 17, and includes a plurality of adjacent trapezoidal leaves 30 which together form an arc of constant radius about the focal spot 18. Each leaf is constructed of a dense radio-opaque material such as lead, tungsten, cerium, tantalum or related alloy.

The leaves 30 are held in sleeves 24 so that each leaf 30 may slide completely within its corresponding sleeve 24 to block the ray 28 associated with that sleeve 24. Preferably, the leaves 30 of the shutter system 22 subtend the entire radiation fan beam to divide the radiation fan beam into a set of adjacent slab-like rays 28 at offset angles f. When the leaf 30 blocks its corresponding ray 28, it is referred to as being in the closed state. The sleeves 24 are of ample length to permit each leaf 30 to slide out of the path of the radiation fan beam so as to leave its corresponding ray 28 completely unobstructed and yet to still be guided by the sleeve 24. In this nonlocking position, a leaf is referred to as being in the "open state".

Each leaf 30 may move rapidly between its open and closed state by means of a primary relay-like electromagnetic actuator 32 connected to the leaf 30 by a slider member 34. The fluence passed by the ray 28 may be controlled by changing the duty cycle of the movement of the leaf that is the ratio of time between which it is in the open state as opposed to the close state.

Figure 2:
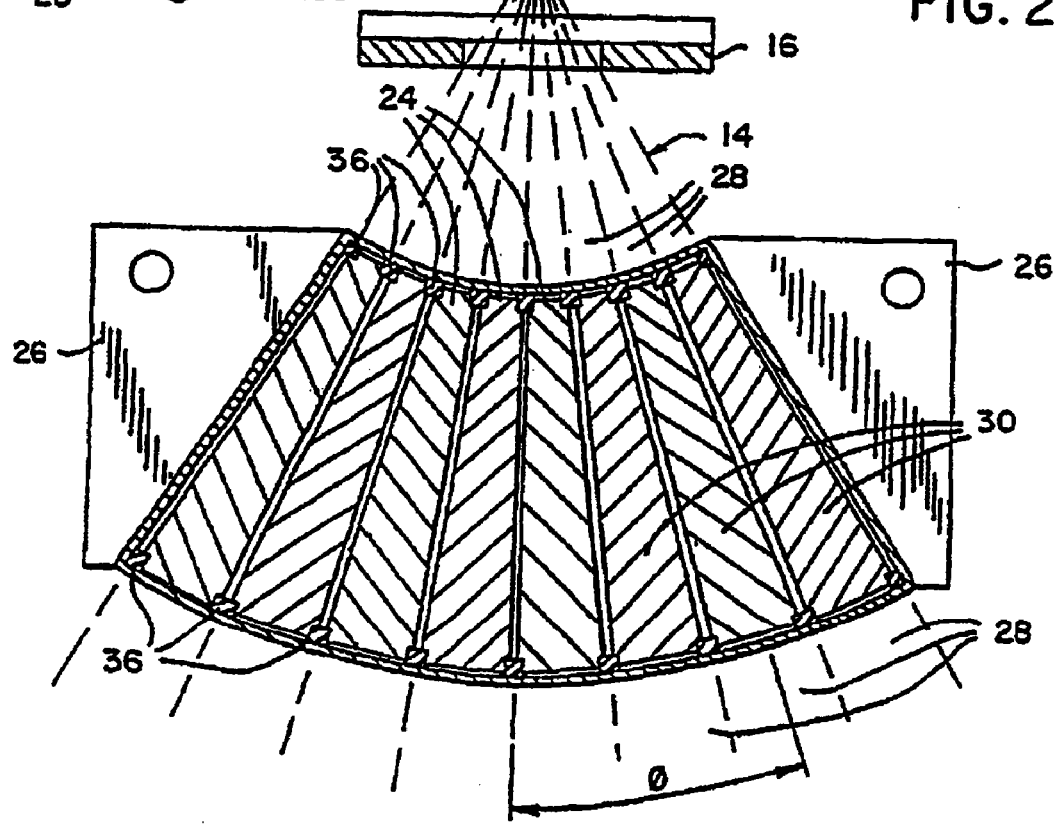
FIG. 2 is a cross section of the shutter system of FIG. 1 along line 2-2 showing the trapezoidal aspect of each shutter leaf for a radiation fan beam of radiation, and the guide rails for supporting the shutter leaves when they move.

Referring to FIG. 2, the leaves 30 are supported and guided within the sleeves 24 by guide tongues 36 fitted into grooves 38 cut along the edges of the leaves 30. The grooves 38 allow the guide tongues 36 to slidably retain the leaves 30 within the sleeves 24 during motion between the open and closed states.

Figure 3:
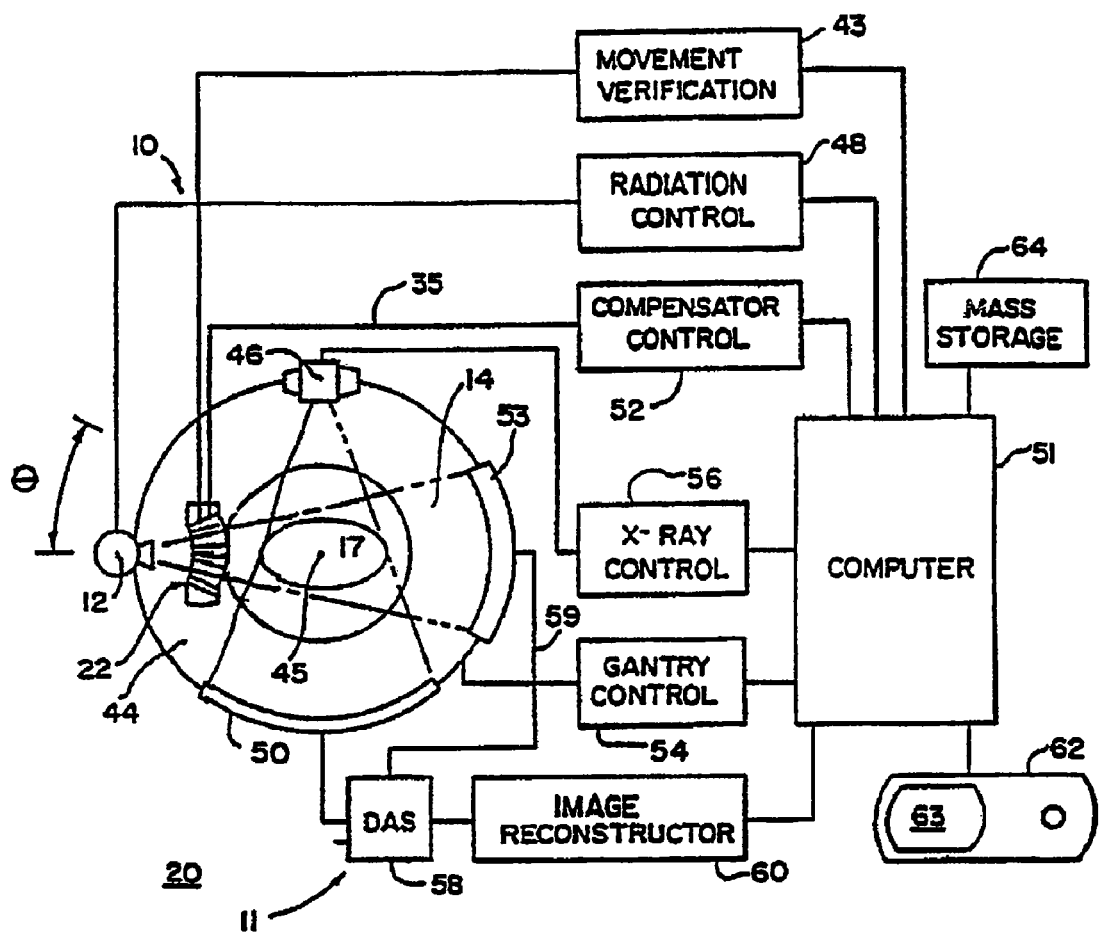
FIG. 3 is a block diagram showing the elements of a radiation therapy machine incorporating a conventional CT scanner and the shutter system and including a computer suitable for controlling that shutter system according to an exemplary embodiment.

Referring now to FIG. 3, the radiation source 12 is mounted on a gantry 44, the latter rotating within the radiation fan beam plane 20 about a center of rotation 45 in the patient 17 so that the radiation fan beam 14 may irradiate a slice of the patient 17 from a variety of gantry angles .theta. The radiation source 12 is controlled by a radiation control module 48 which turns the radiation beam 14 on or off under the control of a computer 51.

A shutter system control 52 directed by a timer generating desired position signals provides electrical excitation to each electromagnet to control, separately, the actuators 32 to move each of the leaves 30 in and out of its corresponding sleeve 24 and ray 38 (see also FIG. 1). The shutter system control 52 moves the leaves 30 of the shutter system 22 rapidly between their open and closed states to either fully attenuate or provide no attenuation to each ray 28. Gradations in the fluence of each ray, as needed for the fluence profile, are obtained by adjusting the relative duration during which each leaf 30 is in the closed position compared to the relative duration during which each leaf 30 is in the open position for each gantry angle.

The ratio between the closed and open states or the "duty cycle" for each leaf 30 affects the total energy passed by a given leaf 30 at each gantry angle and thus controls the average fluence of each ray 28. The ability to control the average fluence at each gantry angle permits accurate control of the dose provided by the radiation beam 14 through the irradiated volume of the patient 17 by therapy planning methods to be described below. The shutter system control 52 also connects with computer 51 to allow program control of the shutter system 22 to be described.

An optional tomographic imaging system 11 employing an x-ray source 46 and an opposed detector array 50 may be advantageously mounted on the same gantry 44 as the radiation source 12 to produce a tomographic or slice image of the irradiated slice of the patient 17 prior to radiation therapy for planning purposes or during treatment. Alternatively, such tomographic imaging may be performed on a separate machine and the slices aligned according to fiducial points on the patient 17.

A gantry control module 54 provides the signals necessary to rotate the gantry 44 and hence to change the position of the radiation source 12 and the gantry angle q of the radiation fan beam 14 for the radiation therapy, as well as for the computer tomography x-ray source 46 and detector array 50 also attached to gantry 44. Gantry control module 54 connects with computer 51 so that the gantry may be rotated under computer control and also to provide the computer 51 with a signal indicating the gantry angle q to assist in that control.

Control modules for the tomographic imaging system 11 include: x-ray control module 56 for turning on and off the x-ray source 46 and data acquisition system 58 for receiving data from the detector array 50 in order to construct a topographic image.

An image reconstructor 60 typically comprising a high speed array processor or the like receives the data from the data acquisition system 58 in order to assist in "reconstructing" a tomographic treatment image from such data according to methods well known in the art. The image reconstructor 60 may also use post-patient radiation detector signals 59 to produce a tomographic absorption image to be used for verification and future therapy planning purposes as described in more detail below.

A terminal 62 comprising a keyboard and display unit 63 allows an operator to input programs and data to the computer 51 and control the radiation therapy machine 10 and the tomographic imaging system 11 and to display images provided by the image reconstructor 60 on display unit 63.

A mass storage system 64, being either a magnetic disk unit or tape drive, allows the storage of data collected by the tomographic imaging system 11 and the post-patient radiation detector 53 for later use. Computer programs for operating the radiation therapy machine 10 will generally be stored in mass storage system 64 and laded into the internal memory of the computer 51 for rapid processing during use of the radiation therapy machine 11.

The radiation source 12 may be a linear accelerator excited in pulsed mode with the pulses in synchrony with the digital to analog converter of the data acquisition system 58 so as a set of views may be obtained during shutter opening and closing. If each projection of radiation at a given gantry angle q during radiotherapy is one second, the pulse rate of linear accelerator may be two hundred times per second providing real-time motion study of movement of the leaves 30 based on the changing fluence exiting the leaf and entering the patient 17.

During operation of the radiation therapy machine 11, the shutter system control 52 receives from the computer 51 a treatment sinogram comprising a fluence profile for each gantry angle θ. The treatment sinogram describes the intensity or fluence of each ray 28 of the radiation beam 14 that is desired for each gantry angle θ at a given position of the patient support table (not shown) as translated through the radiation beam 14.

Figure 4:
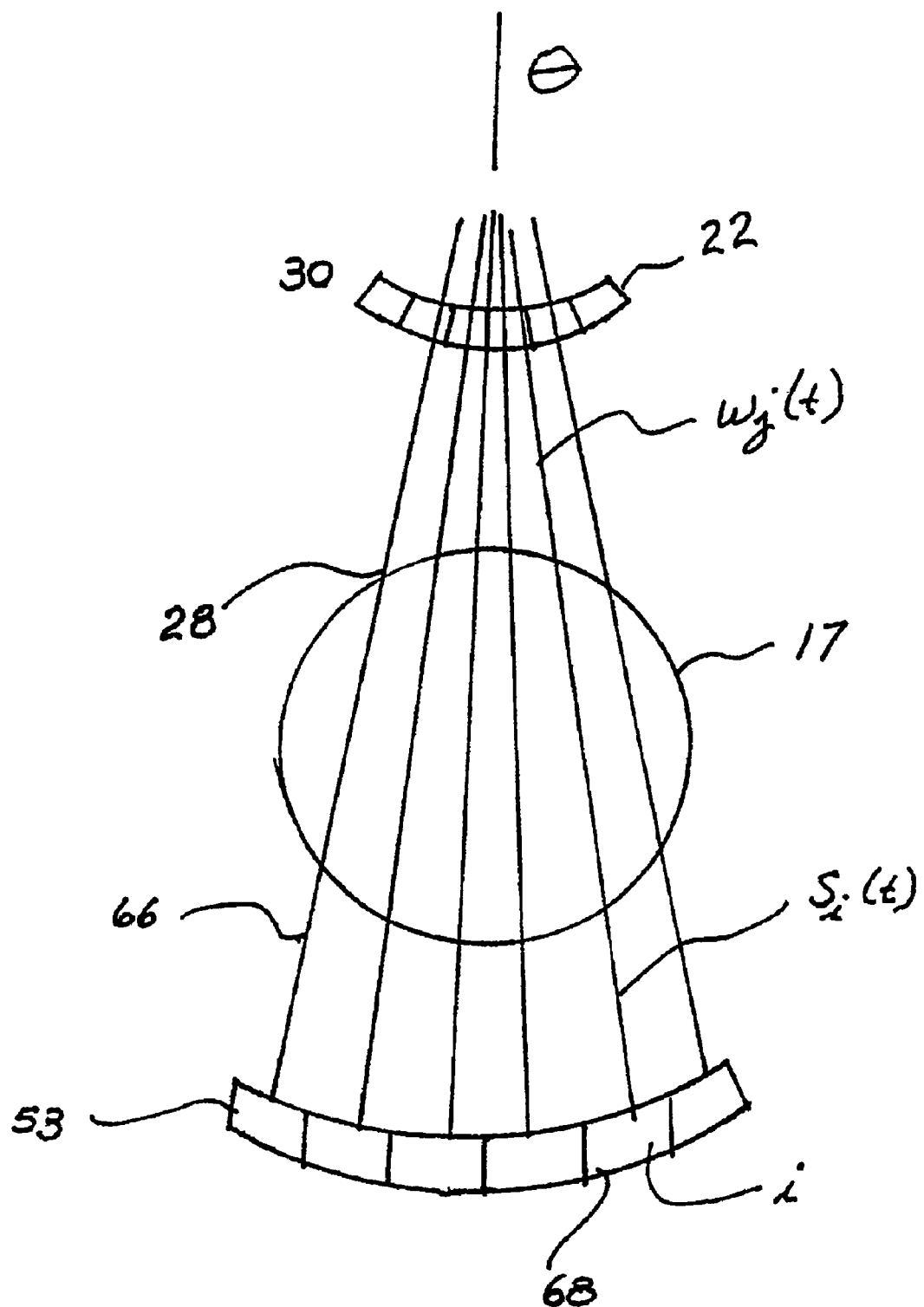
FIG. 4 is a simplified representation of the gantry of the radiation therapy machine of FIG. 3 showing variables used in the calculation of a patient model.

Referring now to FIG. 4, a shutter system provides control of a total number J of 10 rays 28 identified by index variable j=1 to J. Each ray 28 generated by the shutter system 22 passes through the patient 17 along ray center line 66 to be detected by post-patient radiation detector 53 having detector elements.

Treatment Planning

Figure 5:
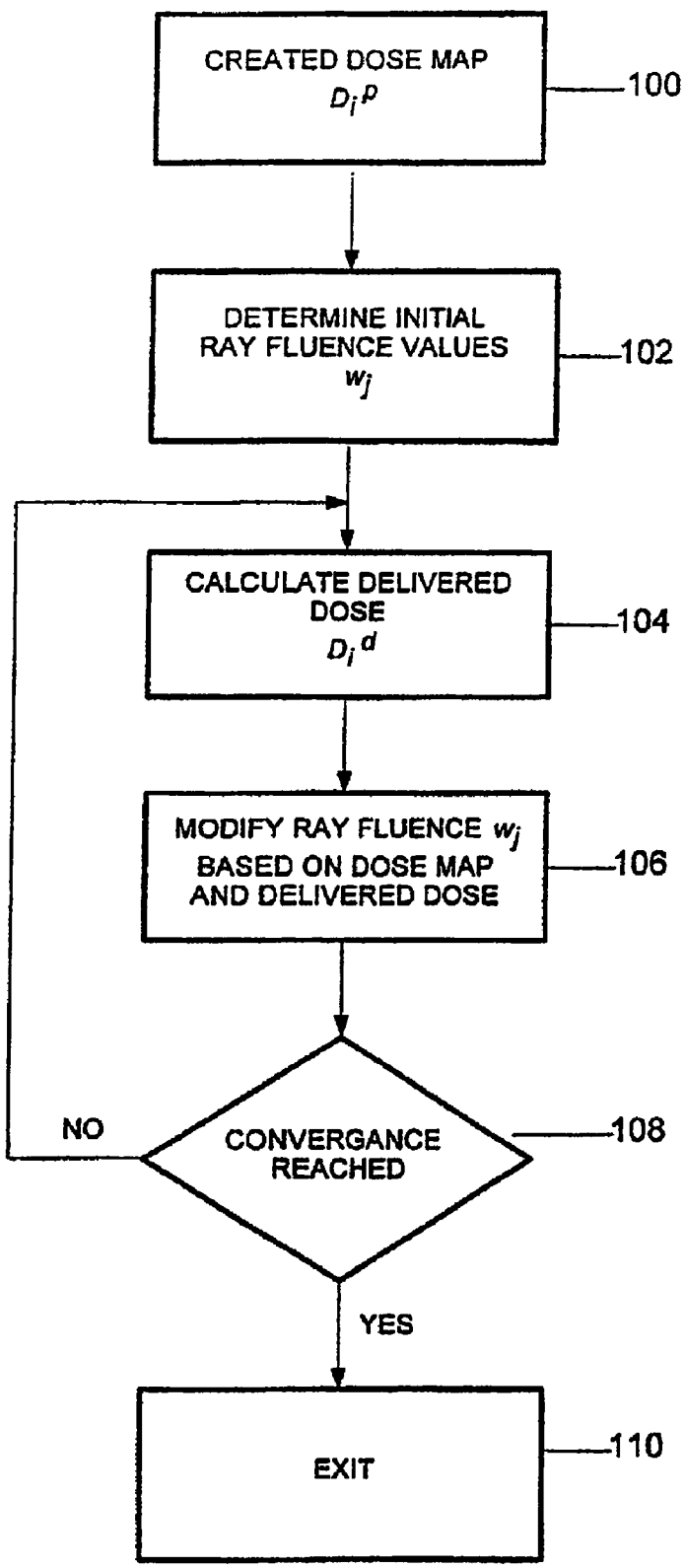
FIG. 5 is a flow diagram for the process of optimization of the ray fluence values per the present invention.

Referring to FIG. 5, the generation of the optimal radiotherapy treatment plan according to the present invention begins with the identification of a prescribed dose map $D_i^p$ providing the amount of dose desired at different voxels i (i=1, . . . , I) within a slice as indicated by process block 100. Typically these different voxels i are grouped into areas that will include one or more areas of tumorous tissue where high dose is required and one or more areas of sensitive tissue where the dose must be limited to below a predetermined value.

The prescribed dose map $D_i^p$ is stored within the memory of the computer as an array of elements, each element holding one digital value. The method for entering the dose map $D_i^p$ may include displaying the tomographic view of the patient on the display of the terminal and manually tracing around the tumorous area using a track-ball or similar input device, as is well understood in the art. Standard area-filling algorithms may be used to transfer the dose values assigned to each trace region to the appropriate element in the array of memory representing the desired dose map. Each element of the dose map $D_i^p$ defines the dose desired at one voxel i within a slice of a patient.

A fluence value $w_j$ of each ray j of each beam at each gantry angle θ that will produce the desired dose at each voxel i must then be determined as indicated by process block 102. This process is one of iteration; an arbitrary initial fluence value $w_j$ for the rays j is selected which is then modified repeatedly until optimized values are obtained.

The closer the initial fluences $w_j$ selected for the rays j are to the final values, the faster the optimization can be completed. For this reason, in one embodiment of the present invention, a library of prior radiotherapy treatment plans is screened to select a treatment plan for treating a patient having a similar arrangement of tumorous tissue and sensitive tissues. The similarity between the patient, the previous treatment plan and the current plan will provide initial fluence values $w_j$ for the rays which are a close approximation to the rays necessary for the current radiotherapy application. The library may consist of several different treatment plans stored within a data storage system, such as a computer, and have a catalog of various treatment volumes of different shapes and sizes.

As represented by process block 104, the delivered dose $D_i^d$ that would be provided by the initial ray fluences $w_j$ is next determined by conventional techniques. As taught in U.S. Pat. No. 5,317,616 issued May 31, 1994, hereby incorporated by reference, a determination of Terma, total energy released per unit mass may be determined along each ray based on the ray's fluence and the properties of the patient. The Terma for a given voxel may be accumulated for each ray and each beam angle and then the total Terma for each voxel convolved with a precomputed scatter kernel(s) to determine dose at that voxel. The kernel(s) may represent the scatter over the range of a beam angle from different beam angles and thus in one convolution operation provides the dose calculation for all beam angles. The kernel(s) may be computed by conventional techniques such as Monte Carlo simulation. The convolution of the Terma with the scatter kernel(s) provides an accurate account of lateral scatter which is of particular importance in cases such as head and neck or tangential-field breast radiotherapy where the irradiated volume is small.

Generally, the Terma of each ray is not saved nor is the partial dose delivered to a voxel by a single ray saved, thus providing substantial memory savings.

At process block 106, the delivered dose $D_i^d$ calculated at process block 104 is compared to the prescribed dose $D_i^p$ entered at process block 100 and each ray's fluence adjusted by an update function relating to a ratio of a function of the prescribed dose $D_i^p$ over a function of the actual dose $D_i^d$ for each voxel i receiving radiation from the given ray j.

In an exemplary embodiment, the update function for modifying the beam weights may be a ratio of the sum at the prescribed dose $D_i^p$ and the motion-uncorrected dose $D_i^d$ for each voxel i (i=1, . . . , I) receiving radiation from the given ray j (j=1, . . . , J), and may be illustrated as follows:

$$w_j^{(k+1)} = w_j^k \frac{\sum_i a D_i^p}{\sum_i a D_i^{dk}}, \quad (1)$$

where $w_j^{(k+1)}$ and $w_j^k$ are the fluence values before and after the modification and a is a predetermined approximation of the dose per energy fluence ($d_{ij}$), or dose per any magnitude related to energy fluence, of the given ray j being modified. Alternatively a may be a non-constant central axis depth dose stored and then looked up to serve as an approximation for $d_{ij}$. By not storing actual values of $d_{ij}$, the memory requirements are still significantly reduced. In the update factor, the inclusion of $d_{ij}$ would normally serve to place the greatest importance on those voxels receiving the highest dose. The approximation used may influence the rate of the conversion rate of the algorithm, but the full dose distribution determined per iteration will maintain the accuracy of a dose computation performed using the convolution/superposition technique.

It can be shown analytically that when this second update method is applied repeatedly per process block 108, (by repeating process blocks 104 and 106 using in each iteration of process block 104 the modified fluence values from the previous process block 106), that the following objective function O(w) tends to reach optimization:

$$O(\vec{w}) = \sum_i (D_i^p - D_i^d)^n \quad (2)$$

where n is an exponent having a value of 2. In a similar approach, O(w) may be optimized using n having value of n>2.

This equation minimizes a sum of the magnitude of the difference between the delivered doses and the prescribed doses. The convex nature of this objective function dictates that any local minimum is also the global minimum. With a convex objective function such as this, the use of stochastic optimization techniques is unwarranted.

The updating method can be further modified to make the objective function more robust. Specifically, the update function can be modified so as to apply weighting factors to each region of the patient, per the following equation:

$$O(\vec{w}) = \sum_m C_m \sum_{i \in \tau_m} (D_i^p - D_i^d)^n \quad (3)$$

In this equation, $C_m$ is a weighting factor assigned to tissue m (m=1, . . . , M), which contains the subset of voxels, $\tau_m$, which can correspond to either tumor or sensitive tissue.

In its application, the penalty for overdosing a voxel in the tumor volume can be set equal to the penalty for underdosing the same voxel. It is straightforward, however, to implement weighting factors that place a greater emphasis on either underdosage or overdosage, thus producing a more clinically acceptable result.

The use of weighting factors is also applicable to sensitive structures. One possibility includes optimization where underdosed voxels are assigned a weight of zero. As a result, the voxels in the sensitive areas are only penalized if they receive a dose greater than the assigned tolerance dose.

Methods for determining radiotherapy treatment plans may be further improved by accounting for patient motion. The effect of patient motion is a consideration that affects dose distributions delivered with IMRT. There are many different factors that may contribute to patient motion. These may include, but are not limited to, daily patient setup uncertainty, internal patient motion due to respiratory, cardiac, and digestive processes, changes in tumor size, changes in patient weight, etc. These factors all contribute to the spatial uncertainty in tumor location throughout the course of a patient's treatment, which may be several weeks in length.

Although FIG. 5 illustrates one exemplary method for generating a radiotherapy treatment plan, it should be understood that multiple such methods exist and may be utilized to provide the advantages described herein.

Figure 6:
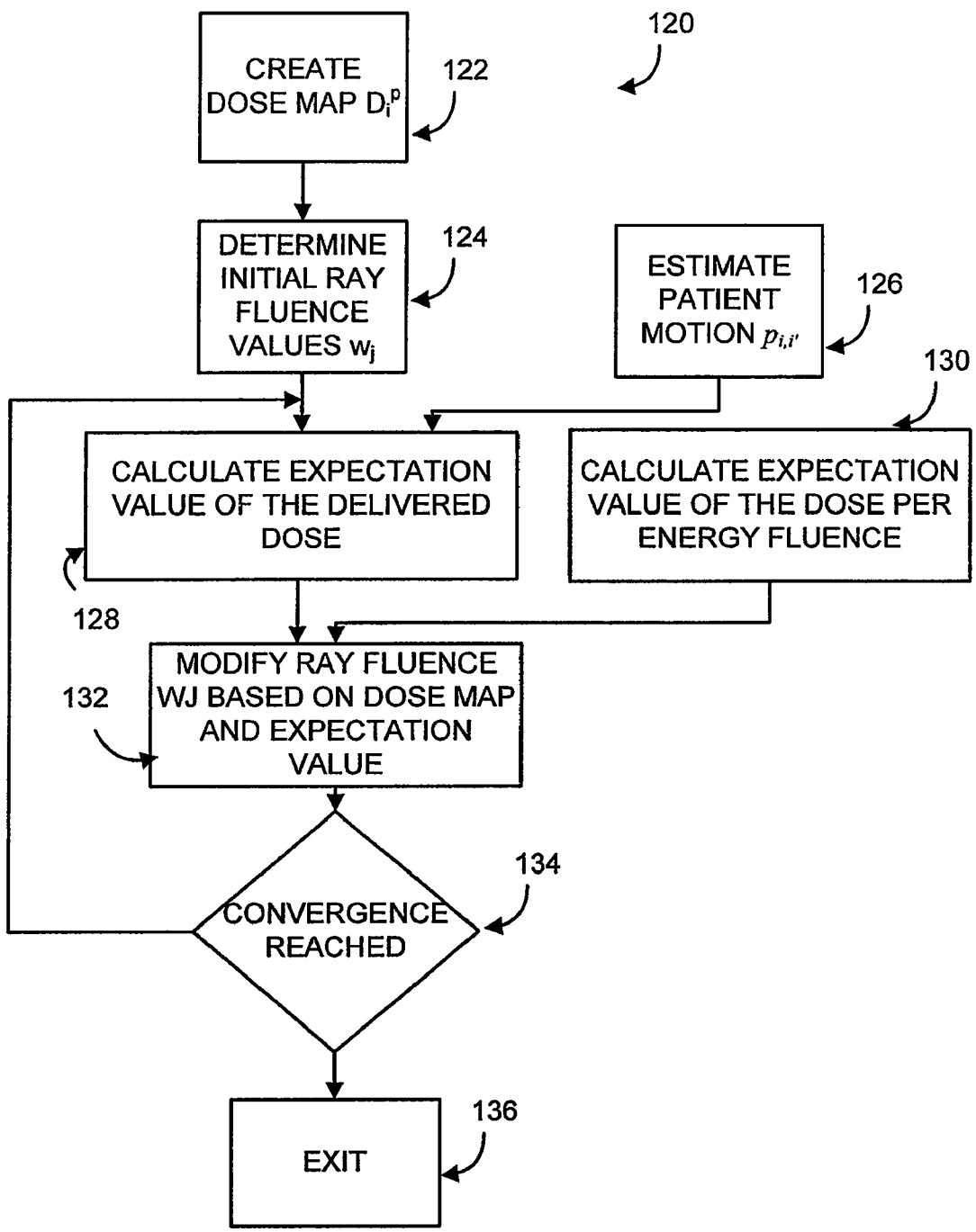
FIG. 6 is a flow diagram for the process of generating an optimal radiotherapy treatment plan including determination of intensity maps for intensity modulated radiation therapy in which the effects of patient motion are taken into account.

Referring to FIG. 6, a flowchart 120 illustrating a method the generation of the optimal radiotherapy treatment plan in a manner that accounts for patient motion is shown, according to an exemplary embodiment. The motion optimized method identifies a prescribed dose map $D_i^p$ 122 and determines a fluence value $w_j$ of each ray j of each beam at each gantry angle θ will produce the desired dose at each voxel i as indicated by process block 124 similar to steps 102 and 104 as described above with reference to FIG. 5 and further described in U.S. Pat. No. 6,560,311 issued May 6, 2003, hereby incorporated by reference.

Concurrently with generation of the ray fluence values patient motion factors can be accounted for using voxel-specific probability distribution functions that describe the probability that the tissue in a given voxel in some time reference image will be located inside some other voxel at a given point in time, as represented by process block 126. Accordingly, in order to extend existing methods to account for patient motion, the expectation value of the objective function is evaluated using a probability distribution functions, as is known in the art. (Unkelbach J, Oelfke U, Phys Med Biol 32, 2471 (2005)). This new objective function may be referred to as a probabilistic objective function. The current application describes a method for minimizing the probabilistic objective function that reduces back to existing methods in the limit of the absence of patient motion.

The pdf, $p_{i,i'}$, is an estimate of the probability of finding the tissue in the voxel that was at location i on the initial simulation day at location i' on a given treatment day. The pdf is always non-negative, and integrates over all i' to unity, for all i. The pdf can be estimated from site-specific imaging information from a representative population of patients, and can be individually tailored for each patient being treated if imaging information is available. Example imaging modalities that can be used to accomplish this are CT, 4D-CT, MRI, or fiducial marker tracking.

Following the estimation of patient motion, as shown in process block 126, the expectation value of the delivered dose, $\langle D_i^d \rangle$ which is a more realistic estimate of the dose distribution that is delivered over the entire treatment course than the motion-uncorrected dose, $D_i^d$, may be calculated as shown by process block 128, using $p_{i,i'}$ as follows:

$$\langle D_i^d \rangle = \sum_{i'} p_{i,i'} D_{i'}^d = \sum_j w_j \sum_{i'} p_{i,i'} d_{i'j} = \sum_j w_j \langle d_{ij} \rangle. \quad (4)$$

Here we have described the motion-uncorrected dose, $D_i^d$, with the relationship: $D_i^d = \Sigma_j d_{ij} w_j$, and the expectation value of the dose per energy fluence $(d_{ij})$ of ray j as:

$$\langle d_{ij} \rangle = \sum_{i'} p_{i,i'} d_{i'j}. \quad (5)$$

Since the expectation value calculation is similar to a convolution operation, $\langle d_{ij} \rangle$ will have a blurred appearance relative to $d_{ij}$. Advantageously, the expectation value calculation models the smearing that occurs in the delivered dose distribution due to patient motion.

The expectation value of the dose per energy fluence, $\langle d_{ij} \rangle$, as shown by process block 130, can be calculated either by (i) application of $p_{i,i'}$ to the pre-calculated $d_{ij}$ values using Equation 5, or (ii) as an operation included in a convolution/superposition dose calculation process via an integration of $p_{i,i'}$ into the scatter kernels. Method (ii) would be more efficient than method (i) if $\langle d_{ij} \rangle$ only needs to be calculated once, for example, if it is assumed that the patient's $p_{i,i'}$ is well modeled by population data. Method (i) would be more efficient than method (ii) if it is determined that $\langle d_{ij} \rangle$ needs to be recalculated more than once for a given patient. This may be required if it is determined midway through the patient's treatment course that the population-based $p_{i,i'}$ is a poor representation of the patient's motion pattern, or if it is determined that $p_{i,i'}$ has changed sufficiently over the patient's treatment course to require an adjustment of the treatment plan.

At process block 132, the expectation value of the delivered dose $D_i^d$, calculated at process block 128 is compared to the prescribed dose $D_i^p$ entered at process block 122 and each ray's fluence adjusted by an update function relating to a ratio of a function of the prescribed dose $D_i^p$ over a function of the actual dose $D_i^d$ for each voxel i receiving radiation from the given ray j.

Patient motion modeled with probability distribution functions can be accounted for in the optimization process with the following iterative scheme:

$$w_j^{(k+1)} = w_j^k \frac{N \sum_{m=1}^M C_m \sum_{i \in \tau_m} \langle d_{ij} \rangle D_i^p}{(N-1) \sum_{m=1}^M C_m \sum_{i \in \tau_m} \langle D_i^{d^k} \rangle \langle d_{ij} \rangle + \sum_{m=1}^M C_m \sum_{i \in \tau_m} \langle d_{ij} D_i^{d^k} \rangle}, \quad (6)$$

where N is the number of treatment fractions, $D_i^p$ is the planned dose to voxel i, $D_i^{d^k}$ is the motion-uncorrected dose to voxel i for iteration k, and $C_m$ is a weighting factor assigned to structure m, which may be either a tumor or sensitive area. The subset of voxel indices contained structure m is $\tau_m$.

It can be shown analytically that the repeated application of the scheme in Equation (6) results in the minimization of the following objective function:

$$O(\vec{w}) = \sum_m \sum_{i \in \tau_m} C_m \langle (D_i^d - D_i^p)^2 \rangle = \sum_m \sum_{i \in \tau_m} C_m \sum_{i'} p_{i,i'} (D_{i'}^d - D_i^p)^2, \quad (7)$$

which is the expectation value of a commonly used quadratic objective function. In Equation (7) it is assumed that the dose is delivered over N treatment fractions, and that the patient motion between treatment fractions is uncorrelated. Following each iteration, a determination may be made whether convergence has been reached, as shown by process blow 134. In convergence is not reached, the iterative process may be repeated. If convergence is reached, the method is concluded, as show by process block 135.

Equation (6) may be an updating function that is modified so as to apply the weighting factors to each region of the patient, further modified to incorporate the patient motion information in the form of expectation values. As was the case with Equation (1), penalties for both overdose and underdose of tumor and sensitive structures can be applied separately with Equation (6) in a straightforward manner.

Referring to the denominator in Equation (6), the quantity $\langle d_{ij} D_i^d \rangle$ is dependent upon the motion-uncorrected dose distribution, and therefore changes with each iteration step. $\langle d_{ij} D_i^d \rangle$ can be either (i) calculated for each iteration step directly using Equation (6), or (ii) the quantity, $$\sum_{i \in \tau_m} \langle d_{ij} D_i^{d^k} \rangle,$$

can be written in terms of $$\lambda_{j,j'} = \sum_{i \in \tau_m} \langle d_{ij}, d_{ij'} \rangle \quad (5)$$

as follows:

$$\sum_{i \in \tau_m} \langle d_{ij} D_i^{d^k} \rangle = \sum_{i \in \tau_m} \langle d_{ij} \sum_{j'} d_{ij'} w_{j'}^k \rangle = \sum_{j'} w_{j'}^k \sum_{i \in \tau_m} \langle d_{ij}, d_{ij'} \rangle = \sum_{j'} w_{j'} \lambda_{j,j'}. \quad (8)$$

The quantity, $\lambda_{j,j'}$, accounts for the coupling between ray j and ray j' in the calculation of Equation (6), and can be pre-calculated prior to the optimization process. The efficiency of each calculation method for $$\sum_{i \in \tau_m} \langle d_{ij} D_i^{d^k} \rangle$$

is dependent upon the number of ray directions, J, the number of iterations, K, and the number of voxels, I, in the problem. The number of operations required for a full optimization, after the initial beamlet calculations, using method (i), is proportional to $I^2 KJ$. For method (ii), the number of operations required to pre-calculate $\lambda_{j,j'}$ is proportional to $I^2 J^2$, and the operations required to do the optimization is then proportional to KI. The pre-calculation time for method (ii) can be a substantially higher price to pay than that of method (i), however, especially when J is much greater than K, which is often the case. For example, helical tomotherapy optimizations often require 500 iterations (K) and around 10,000 beam directions (J). For such a case, method (ii) would take longer than method i by a factor of J/K=20.

It is specifically intended that the present invention not be limited to the embodiments and illustrations contained herein, but include modified forms of those embodiments including portions of the embodiments and combinations of elements of different embodiments as come within the scope of the following claims.

We claim:

1. A computer-implemented method for optimizing a radiation treatment plan for a radiotherapy machine providing independently controlled radiation along a plurality of rays j directed toward a patient configured to account for the effects of patient motion, comprising:
   a) generating a probability distribution function quantitatively expressing patient motion;
   b) identifying a prescribed total dose $D_i^p$ at the voxels i in a treatment area;
   c) assigning a fluence value $w_j$ for each ray j, based on an iterative function:

$$w_j^{(k+1)} = w_j^k \frac{N \sum_{m=1}^{M} C_m \sum_{i \in \tau_m} \langle d_{ij} \rangle D_i^p}{(N-1) \sum_{m=1}^{M} C_m \sum_{i \in \tau_m} \langle D_i^{d^k} \rangle \langle d_{ij} \rangle + \sum_{m=1}^{M} C_m \sum_{i \in \tau_m} \langle d_{ij} D_i^{d^k} \rangle}, \quad (6)$$

where N is the number of treatment fractions, $D_i^p$ is the planned dose to voxel i, $D_i^{d^k}$ is the motion-uncorrected dose to voxel i for iteration k, and $C_m$ is a weighting factor assigned to structure m, which may be either a tumor or sensitive area;
   d) calculating an actual total dose $D_i^d$ produced in each voxel i within the assigned fluence values of step (c); and
   e) calculating an expectation value of the dose per energy fluence, $\langle d_{ij} \rangle$ based on the actual total dose $D_i^d$ and the probability distribution function.

2. The method of claim 1, further including calculating an expectation value of the delivered dose $\langle D_i^d \rangle$ based on an aggregation of the expectation value of the dose per energy fluence, $\langle d_{ij} \rangle$.

3. The method of claim 1, wherein the probability distribution function is generated based on at least one of calculated daily patient set up uncertainty, quantified internal patient motion due to respiratory, cardiac, and/or digestive processes, detected changes in tumor size, and detected changes in patient weight.

4. The method of claim 1, wherein the probability distribution function is generated based on a correlation between one or more attributes of the patient and a representative population of patients.

5. The method of claim 1, wherein the probability distribution function is generated based on one or more detected attributes of the patient.

6. The method of claim 5, wherein the attributes of the patient are detected based on at least one of computed tomography imaging, the four dimensional computed tomography imaging, magnetic resonance imaging, and fiducial marker tracking.

7. The method of claim 1, wherein calculating expectation value of the dose per energy fluence, $\langle d_{ij} \rangle$ may be implemented via an integration of $p_{i,i'}$ into the scatter kernels.

8. A system for optimizing a radiation treatment plan by providing independently controlled radiation along a plurality of rays j directed toward a patient configured to account for the effects of patient motion, comprising:
   a radiation source configured to generate the plurality of rays;
   a shutter system configured to attenuate the rays generated by the radiation source; and
   a computer system configured to control the radiation source and the shutter system to implement a radiation treatment plan to account for the effects of patient motion, including the steps of
   a) generating a probability distribution function quantitatively expressing patient motion;
   b) identifying a prescribed total dose $D_i^p$ at the voxels i in a treatment area;
   c) assigning a fluence value $w_j$ for each ray j, based on an iterative function:

$$w_j^{(k+1)} = w_j^k \frac{N \sum_{m=1}^{M} C_m \sum_{i \in \tau_m} \langle d_{ij} \rangle D_i^p}{(N-1) \sum_{m=1}^{M} C_m \sum_{i \in \tau_m} \langle D_i^{d^k} \rangle \langle d_{ij} \rangle + \sum_{m=1}^{M} C_m \sum_{i \in \tau_m} \langle d_{ij} D_i^{d^k} \rangle}, \quad (6)$$

where N is the number of treatment fractions, $D_i^p$ is the planned dose to voxel i, $D_i^{d^k}$ is the motion-uncorrected dose to voxel i for iteration k, and $C_m$ is a weighting factor assigned to structure m, which may be either a tumor or sensitive area;

d) calculating an actual total dose $D_i^d$ produced in each voxel i within the assigned fluence values of step (c); and e) calculating an expectation value of the dose per energy fluence, $\langle d_{ij} \rangle$ based on the actual total dose $D_i^d$ and the probability distribution function.

9. The system of claim 8, wherein the steps further include calculating an expectation value of the delivered dose $\langle D_i^d \rangle$ based on an aggregation of the expectation value of the dose per energy fluence, $\langle d_{ij} \rangle$.

10. The system of claim 8, wherein the probability distribution function is generated based on at least one of calculated daily patient set up uncertainty, quantified internal patient motion due to respiratory, cardiac, and/or digestive processes, detected changes in tumor size, and detected changes in patient weight.

11. The system of claim 8, wherein the probability distribution function is generated based on a correlation between one or more attributes of the patient and a representative population of patients.

12. The system of claim 8, wherein the probability distribution function is generated based on one or more detected attributes of the patient.

13. The system of claim 12, wherein the attributes of the patient are detected based on at least one of computed tomography imaging, the four dimensional computed tomography imaging, magnetic resonance imaging, and fiducial marker tracking.

14. The system of claim 8, wherein calculating expectation value of the dose per energy fluence, $\langle d_{ij} \rangle$ may be implemented via an integration of $p_{i,i'}$ into the scatter kernels.

15. A computer-implemented method for optimizing a radiation treatment plan for a radiotherapy machine providing independently controlled radiation along a plurality of rays j directed toward a patient configured to account for the effects of patient motion, comprising:

a) generating a probability distribution function quantitatively expressing patient motion;

b) identifying a prescribed total dose $D_i^p$ at the voxels i in a treatment area;

c) assigning a fluence value $w_j$ for each ray j, based on an iterative function:

$$w_j^{(k+1)} = w_j^k \frac{N \sum_{m=1}^{M} C_m \sum_{i \in \tau_m} \langle d_{ij} \rangle D_i^p}{(N-1) \sum_{m=1}^{M} C_m \sum_{i \in \tau_m} \langle D_i^{d^k} \rangle \langle d_{ij} \rangle + \sum_{m=1}^{M} C_m \sum_{i \in \tau_m} \langle d_{ij} D_i^{d^k} \rangle}, \quad (6)$$

where N is the number of treatment fractions, $D_i^p$ is the planned dose to voxel i, $D_i^{d^k}$ is the motion-uncorrected dose to voxel i for iteration k, and $C_m$ is a weighting factor assigned to structure m, which may be either a tumor or sensitive area; and d) calculating an expectation value of the dose per energy fluence, $\langle d_{ij} \rangle$ based on the actual total dose $D_i^d$ and the probability distribution function produced in each voxel i within the assigned fluence values of step (c).

16. The method of claim 15, further including calculating an expectation value of the delivered dose $\langle D_i^d \rangle$ based on an aggregation of the expectation value of the dose per energy fluence, $\langle d_{ij} \rangle$.

17. The method of claim 15, wherein the probability distribution function is generated based on a correlation between one or more attributes of the patient and a representative population of patients.

18. The method of claim 15, wherein the probability distribution function is generated based on one or more detected attributes of the patient.

19. The method of claim 18, wherein the attributes of the patient are detected based on at least one of computed tomography imaging, the four dimensional computed tomography imaging, magnetic resonance imaging, and fiducial marker tracking.

20. The method of claim 15, wherein calculating expectation value of the dose per energy fluence, $\langle d_{ij} \rangle$ may be implemented via an integration of $p_{i,i'}$ into the scatter kernels.

* * * * *